United States Patent
Caron et al.

(10) Patent No.: US 7,864,321 B2
(45) Date of Patent: Jan. 4, 2011

(54) EVANESCENT WAVE MULTIMODE OPTICAL WAVEGUIDE SENSOR WITH CONTINUOUS REDISTRIBUTION OF OPTICAL POWER BETWEEN THE MODES

(75) Inventors: Serge Caron, Saint-Augustin-de-Desmaures (CA); Lia Mouslinkina, Québec (CA); Claude Pare, Saint-Augustin-de-Desmaures (CA); André Fougeres, Québec (CA)

(73) Assignee: Institut National D'Optique, Quebec, QC (CA)

( * ) Notice: Subject to any disclaimer, the term of this patent is extended or adjusted under 35 U.S.C. 154(b) by 247 days.

(21) Appl. No.: 11/757,584

(22) Filed: Jun. 4, 2007

(65) Prior Publication Data

US 2008/0297799 A1    Dec. 4, 2008

(51) Int. Cl.
   *G01N 15/06* (2006.01)
(52) U.S. Cl. .................. 356/432; 385/144; 250/227.14
(58) Field of Classification Search ................ 356/432; 385/144–145; 250/227.14–227.19
   See application file for complete search history.

(56) References Cited

U.S. PATENT DOCUMENTS

| | | | | |
|---|---|---|---|---|
| 4,893,894 A * | 1/1990 | Caimi | ........................ | 385/12 |
| 5,164,588 A * | 11/1992 | Marcus | .................. | 250/227.21 |
| 5,239,176 A * | 8/1993 | Stevenson | .............. | 250/227.25 |
| 5,525,800 A | 6/1996 | Sanghera et al. | | |
| 6,198,861 B1 * | 3/2001 | Kellar et al. | ................... | 385/30 |
| 7,167,615 B1 * | 1/2007 | Wawro et al. | ................. | 385/37 |

2003/0217920 A1    11/2003  Peper et al.

FOREIGN PATENT DOCUMENTS

WO            0054039            9/2000

OTHER PUBLICATIONS

Inagawa, Ikuo et al. "Temperature Dependence of Transmission Loss of Chalcogenide Glass Fibers", Japanese Journal of Applied Physics 36 (1997) p. 2229-2235.*
Kurt Seiler, "Ion-Selective Optode Membranes", Fluka Chemie AG, CH-9470 Buchs, 1993.
N. J. Harrick, "Internal Reflection Spectroscopy", Harrick Scientific Corporation, Ossining, NY, 1979, pp. 89, 90, 92-145.
F. P. Payne et al., "Deviation from Beer's law in multimode optical fiber evanescent field sensors", International Journal of Optoelectronics, vol. 8, pp. 743-748, Cambridge University Engineering Department, England, 1993.

(Continued)

*Primary Examiner*—Gregory J Toatley
*Assistant Examiner*—Rebecca C Slomski
(74) *Attorney, Agent, or Firm*—Ogilvy Renault LLP

(57) ABSTRACT

There is provided an evanescent wave multimode optical waveguide sensitive to a chemical species or to a physical parameter. The optical waveguide comprises a core and a cladding having a cladding refractive index lower than that of the core for guiding light to be propagated in the optical waveguide. The cladding defines with the core an optical waveguide providing mode coupling. A chemical indicator is provided in the cladding for causing a variation of the optical absorption of the cladding as a function of the chemical species or the physical parameter. The cladding is interrogated by the evanescent wave of the propagated light. The mode coupling causes unabsorbed light power to be redistributed among the multiple modes while light propagates along the optical waveguide.

15 Claims, 8 Drawing Sheets

OTHER PUBLICATIONS

S. Savovic et al., "Method for calculating the coupling coefficient in step-index optical fibers", Applied Optics, 46, 1477, 2007.

V. Rudy et al., "Evanescent wave absorption spectroscopy using multimode fibers", School of Physical Sciences, Dublin City University, Glasnevin, Dublin 9, Ireland, 1990, J. Appl. Phys. vol. 67, No. 10, pp. 6070-6074.

I. Pierrejean et al., "Effects of structural anomalies of the PMMA core in the plastic optical fibers", First Plastic Optical Fibres and Applications Conference, held in Paris, France, Jun. 22-23, 1992, pp. 96-100.

Michael D. Degrandpre et al., "Long Path Fiber-Optic Sensor for Evanescent Field Absorbance Measurements", Center for Process Analytical Chemistry, Department of Chemistry, BG-10, University of Washington, Seattle, Washington, 1988, Analytical Chemistry, vol. 60, No. 23, pp. 2582-2586.

H. Tai et al., "Fiber-optic evanescent-wave methane-gas sensor using optical absorption for the 3.392-um line of a He-Ne laser", Research and Development Institute, Optics Letters, vol. 12, No. 6, pp. 437-439, Jun. 1987.

D. Gloge, "Weakly Guiding Fibers", Bell Telephone Laboratories, Inc., Crawford Hill Laboratory, Holmdel, NJ, Applied Optics, vol. 10, No. 10, Oct. 1971, pp. 2252-2258.

P. G. Lye et al., "Investigating the sensitivity of PMMA optical fibres for use as an evanescent field absorption sensor in aqueous solutions", Institute of Physics Publishing, Journal of Physics: Conference Series 15 (2005), pp. 262-269.

* cited by examiner

EVANESCENT WAVE MULTIMODE OPTICAL WAVEGUIDE SENSOR WITH CONTINUOUS REDISTRIBUTION OF OPTICAL POWER BETWEEN THE MODES

BACKGROUND OF THE INVENTION

1. Field of the Invention

The present invention relates to evanescent wave optical waveguide sensors for measuring chemical or physical parameters. More particularly, the present invention relates to chemical sensors and more specifically to ion-selective sensors.

2. Background Art

Chemical sensors are used in various applications including environmental emission control, agri-food industry, and other industrial applications. They are also used in biomedical applications and clinical analysis for determining the pH, the presence of specific ions or the oxygen or alcohol concentration in a sample solution for example. Optical chemical analysis methods include, for example, Fourier transform infrared spectroscopy.

Optical fiber based optodes generally use a sensing membrane deposited at the fiber tip which was previously cleaved and polished. Alternatively, evanescent wave spectroscopy uses an optical waveguide that is immersed into the sample solution. Light is guided in the waveguide by internal reflection at the waveguide-solution interface. The refractive index of the waveguide is higher than that of the solution so that the solution acts as a cladding for the optical waveguide. Light is mostly propagated in the waveguide but part of the light, namely the evanescent wave, propagates in the solution (acting in a way similar to a waveguide cladding) and can then be absorbed by the analyte. Analysis of the measured absorption spectra provides an indication of the presence of given chemicals.

The use of a polymer membrane cladding on an optical waveguide was also proposed as an alternative design of the evanescent wave sensor. In this case, the analyte diffuses in the membrane when the optical waveguide is immersed in the sample solution. As light is guided by the core, the evanescent wave propagates in the polymer membrane and the optical absorbance of the analyte which diffused in the cladding is measured.

In conventional multimode optical waveguides, distribution of the optical power between the core and the cladding is different for each mode. Low-order modes are much confined in the core of the fiber compared to high-order modes, the latter interacting more strongly with the cladding or surrounding sample solution. The high-order modes are then depleted rapidly by evanescent wave absorption compared to the low-order modes. The waveguide optical absorbance is therefore not proportional to that of the cladding, the absorbance being defined as minus the logarithm of the light transmittance of a material or a device. Accordingly, in Payne, F. P. and Z. M. Hale, "Deviation from Beer's law in multimode optical fiber evanescent field sensors.", International Journal of Optoelectronics, 8, 743, 1993, it was demonstrated that the Beer-Lambert law, which linearly relates the absorbance of an optical waveguide to the concentration of an absorbing species in the cladding or in a surrounding solution is inapplicable in the case of evanescent wave spectroscopy with multimode fibers. Reliable quantification of the concentration of the absorbing species is therefore not straightforward. It is noted that the Beer-Lambert law usually applies to light propagating through a flat medium and says that the absorbance of the medium is proportional to the concentration of the absorbing chemicals it contains and to the light propagation length in the medium.

SUMMARY OF INVENTION

It is therefore an aim of the present invention to provide an evanescent wave sensing optical waveguide and sensor that overcome some of the drawbacks of the prior art.

According to one aspect of the invention, there is provided an evanescent wave multimode optical waveguide for use as an optode. The sensing waveguide combines a multimode optical waveguide with high mode coupling and with a cladding having an optical absorption varying with a chemical or a physical parameter to be sensed and interrogated by means of the evanescent wave. The proposed optode allows absorbance-based chemical analysis not only in colorless and transparent solutions but also in colored and turbid ones without any need to provide mechanical filtration of the sample in a close proximity to the sensing element (e.g. dialysis membranes).

According to another aspect of the invention, there is provided an evanescent wave multimode optical waveguide sensitive to a chemical species or to a physical parameter. The optical waveguide comprises a core and a cladding having a cladding refractive index lower than that of the core for guiding light to be propagated in the optical waveguide. The cladding defines with the core an optical waveguide providing mode coupling. A chemical indicator is provided in the cladding for causing a variation of the optical absorption of the cladding as a function of the chemical species or the physical parameter. The cladding is interrogated by the evanescent wave of the propagated light. The mode coupling causes unabsorbed light power to be redistributed among the multiple modes while light propagates along the optical waveguide.

For example, an ion-selective optical fiber sensor is prepared from a polymer optical fiber (POF) and a cladding of a conventional polymeric ion-selective coating. A high mode coupling arises from micro-heterogeneities of the POF core material (poly(methyl methacrylate) (PMMA) for example). The variable optical absorption property is provided by the sensing cladding containing a specific chemical indicator (i.e., a dye) directly or indirectly selectively sensitive to the target ion to be analyzed.

It is noted that the indicator refers herein to any compound that changes its optical absorption spectrum according to the chemical equilibrium it establishes with its surrounding environment. It can be organic, organometallic or inorganic. Quantum dots can also be considered as indicators as well as polymer semiconductors.

The proposed sensing principle is extended further for measuring various chemical species or physical parameters detected optically through a change of the optical absorption spectrum of the sensing cladding by thermochromism (temperature), solvatochromism (solvent vapor detection), electrochromism (current), ionochromism (ion), halochromism (pH), and piezochromism (pressure), etc.

While light propagates in the optical waveguide with a sensing cladding, it remains confined in the core and the evanescent wave propagates in the sensing cladding generating the optode response. Thus, the proposed evanescent wave optical waveguide can be used in colored and turbid sample solutions since light does not propagate in the non-transparent solution.

In conventional low mode coupling waveguides, high-order modes interact more strongly with the sensing cladding or surrounding sample solution than the low-order modes, resulting in the high-order modes to be depleted rapidly along the waveguide due to evanescent wave absorption. As a consequence, the waveguide optical absorbance is not proportional to that of the cladding. On the contrary, a strong mode coupling in the optical waveguide results in the replenishing of the high-order modes via mode mixing, i.e. the optical power is continuously redistributed among the modes while light propagates along the waveguide. This in turn leads to a linear dependence of the absorbance of the sensing waveguide on that of the sensing cladding, the latter following a Beer-Lambert law. Consequently, the absorbance of the cladding being proportional to the concentration of a given state of the indicator within the cladding, there is a relation similar to a Beer-Lambert law between the concentration of the dye (in this state) and the optical waveguide absorbance, and the sensing waveguide can be used reliably for quantitative analysis.

Moreover, a strong mode coupling results in an absorbance independence on the light injection conditions at the input of the waveguide, which provides stability of the sensor to light injection conditions between the light source the sensing waveguide and between the sensing waveguide and the detector. Similarly, the sensor is less sensitive to vibrations, movements and bending of the sensing optical fiber.

There is provided an evanescent wave multimode optical waveguide sensitive to a chemical species or to a physical parameter. The optical waveguide comprises an optical waveguide core having a core refractive index and a cladding surrounding the core and having a cladding refractive index lower than the core refractive index for guiding light to be propagated in the optical waveguide such that an evanescent wave of light propagates in the cladding. The cladding defines with the core an optical waveguide providing mode coupling such that multiple modes of the propagated light are coupled while light propagates along the optical waveguide. A chemical indicator is provided in the cladding. The indicator causing a variation of the optical absorption of the cladding as a function of the chemical species or the physical parameter. The evanescent wave propagating in the cladding resulting in light to be at least partly absorbed by the indicator. The mode coupling causing unabsorbed light power to be redistributed among the multiple modes while light propagates along the optical waveguide.

According to another aspect of the invention, mode coupling provides that the absorbance of the sensing waveguide depends linearly on the concentration of the absorbing species within its cladding, leading to a relation similar to a Beer-Lambert law.

According to another aspect of the invention, there is provided an evanescent wave multimode optical waveguide sensor for measuring a chemical species or a physical parameter. The sensor comprises a portion of an optical waveguide having an optical waveguide core and a cladding surrounding the core having a refractive index lower than that of the core for guiding light to be propagated in the optical waveguide such that an evanescent wave of the light propagates in the cladding. The cladding has an optical absorption varying with the chemical species or the physical parameter. The evanescent wave is partially absorbed by the cladding from the optical absorption. The optical waveguide has a mode coupling length which is substantially less than a sensing length of the optical waveguide for providing mode coupling of light power between multiple modes of the propagated light. A light source unit is connected to the optical waveguide for providing the light to be propagated in the optical waveguide. A detection unit is connected to the optical waveguide for detecting the light propagated in the optical waveguide for determining an optical absorbance of the light in the optical waveguide. A processing unit is associated with the detection unit for determining the chemical species or the physical parameter from the determined optical absorbance.

According to another aspect of the invention, there is provided a method for determining a concentration of a chemical species in a sample solution or a physical parameter. The method comprises: providing an optical waveguide having an optical waveguide core and a cladding for guiding light to be propagated in the optical waveguide; propagating light in the optical waveguide such that mode coupling occurs in the optical waveguide while the light propagates, an evanescent wave of the light propagating in the cladding to be partially absorbed by the cladding; exposing the optical waveguide to the sample solution or to the physical parameter to produce a variation of an optical absorption of the cladding; detecting light propagated in the optical waveguide; determining an optical absorbance in the optical waveguide from the detected light; quantifying the concentration of the chemical species or the physical parameter from the determined optical absorbance; and outputting the quantified concentration of the chemical species or the quantified physical parameter.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DESCRIPTION OF THE PREFERRED EMBODIMENTS

Figure 1:
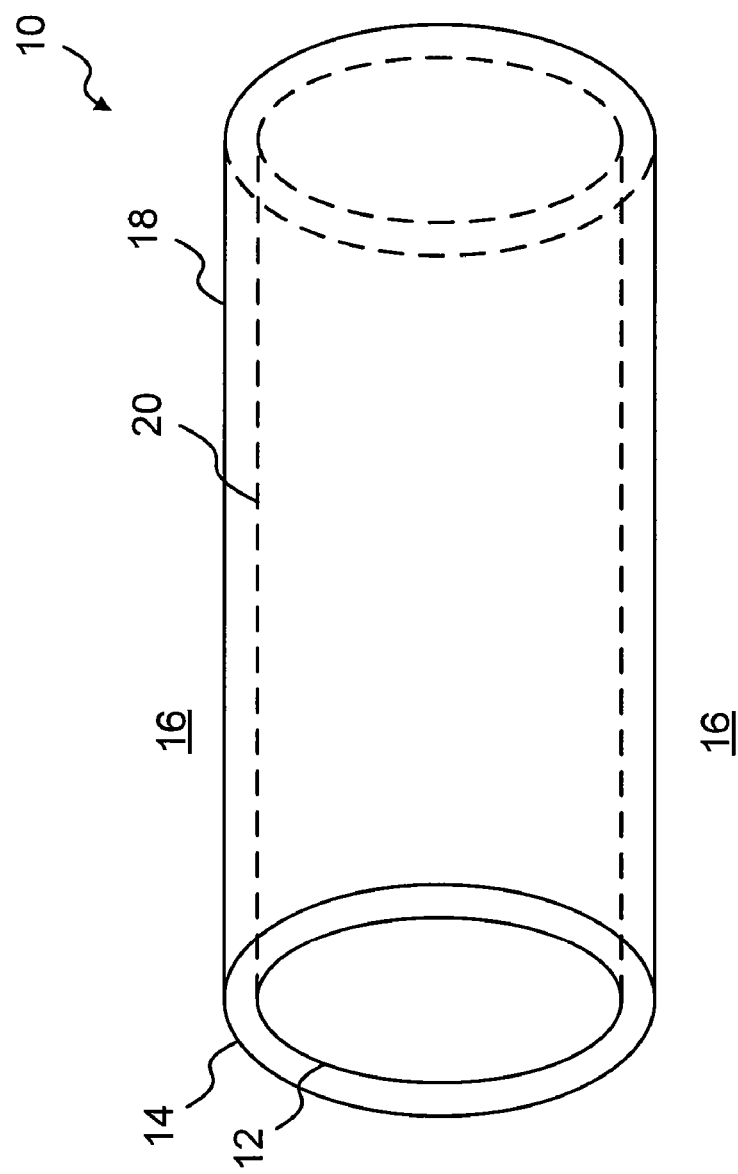
FIG. 1 is a schematic view illustrating an evanescent wave multimode optical fiber, in accordance with one embodiment of the invention.

Now referring to the drawings, FIG. 1 illustrates an evanescent wave multimode optical fiber 10. The optical fiber 10 has a multimode core 12 and a sensing cladding 14 surrounding the core 12. The core 12 is made of a substantially heterogeneous material so as to provide high mode coupling. In this embodiment, the optical fiber 12 is a plastic optical fiber (POF) and the core 12 is made of poly(methyl methAcrylate)

(PMMA), such as Plexiglas®. In this case, mode coupling is provided in the optical fiber by optical scattering within the core material. Any other material providing a high structural or microscopic heterogeneity resulting in high mode coupling in the multimode optical fiber 10 could be used as well in the fiber core 12. Instead of using a heterogeneous material, high mode coupling in the multimode optical fiber 10 can be otherwise achieved by providing structural irregularities along the fiber in the core 12 or the cladding 14.

Different mechanisms can be used to induce a mode coupling within an optical fiber. For example, high mode coupling can be produced by providing inhomogeneities, such as material impurities associated with the manufacturing process, multiple micro-deformations in the core material, micro-bends of the optical fiber, an irregular core-cladding interface, refractive index fluctuations, or macrodefects, curvatures or macrocracks caused by fiber aging, and/or long-duration bending stress or high pressures. Creating such inhomogeneities in the cladding can also provide high mode coupling. As such, irregularities in the optical fiber 10 can be provided by any means which causes the refractive indices of the optical fiber 10 to vary along the fiber 10 to provide mode coupling. It is noted that the numerical aperture of the optical fiber also influences the mode coupling length. A higher numerical aperture implies a larger number of propagation modes, and a longer fiber length is then required to complete the coupling between all of the modes.

The sensing cladding 14 comprises a chemical indicator. Therefore, in addition to stable intrinsic core attenuation losses, light propagating in the fiber is absorbed via the evanescent field which interacts with the cladding 14. In this embodiment, the fiber 10 is sensitive to a given chemical or chemicals in a sample solution 16 in which the optical fiber 10 is immersed, but it is noted that in other embodiments the indicator could be sensitive to a physical parameter to be measured.

The sensing cladding 14 has a refractive index lower than that of the core 12 so that light propagated in the optical fiber 10 is guided by total internal reflection at the core-cladding interface 20. The sensing cladding 14 is also selected to have sufficient mechanical adhesion to the material of the core 12.

When the ion-selective sensing optical fiber 10 is immersed into a sample solution 16, a reversible chemical equilibrium is established between the cladding 14 and the sample solution 16. As will be discussed hereinbelow, for ions sensing, the absorption spectrum of the optical fiber 10 is related to the relative concentration of protonated and deprotonated forms of the dye indicator. Accordingly, the sensing optical fiber 10 can be used as a quantitative sensor by allowing determination of the degree of deprotonation (1−x) of the indicator.

When the optical fiber 10 having a thin ion-selective cladding 14 is immersed in an aqueous sample solution 16 (refractive index of about 1.333), the resulting configuration can be viewed as a double-clad fiber, the cladding 14 providing a first clad layer and the water solution 16 providing a second clad layer. In terms of geometrical optics, some of the rays are guided via total internal reflections at the cladding-solution interface 18. Those rays are rapidly attenuated as they suffer strong absorption due to multiple passages through the cladding 14. Accordingly, the optical power detected at the output of the optical fiber 10 only comes from optical modes guided by total internal reflection at the core-cladding interface 20. For optical wavelengths within the absorption spectrum of the dye indicator, a model assuming a cladding 14 of infinite thickness is thus justified. The optical fiber 10 is therefore considered as a single-clad fiber.

The optical fiber 10 is largely multimode. This implies that either a ray tracing or a modal analysis model can be used. According to both models, the Beer-Lambert law that relates, for instance, the concentrations of the protonated and deprotonated states of the dye indicator in the cladding to the optical absorbance of the optical fiber at a given wavelength would not be valid if the optical fiber showed low mode coupling, as it is the case for high optical quality optical fibers. When light propagates along such low mode coupling optical fibers, higher-order modes show an evanescent wave that extends further into the cladding and they are consequently more attenuated than the low-order modes. The proportion of optical power propagating in high-order modes should decrease and the absorption rate should decrease accordingly. On the contrary, the Beer-Lambert law assumes a uniform absorption rate. However, it can be shown that the Beer-Lambert law is justified in the case of strong mode coupling such as mode coupling provided by the heterogeneous core 12 of the optical fiber 10.

Payne and Hale's Model

Figure 2:
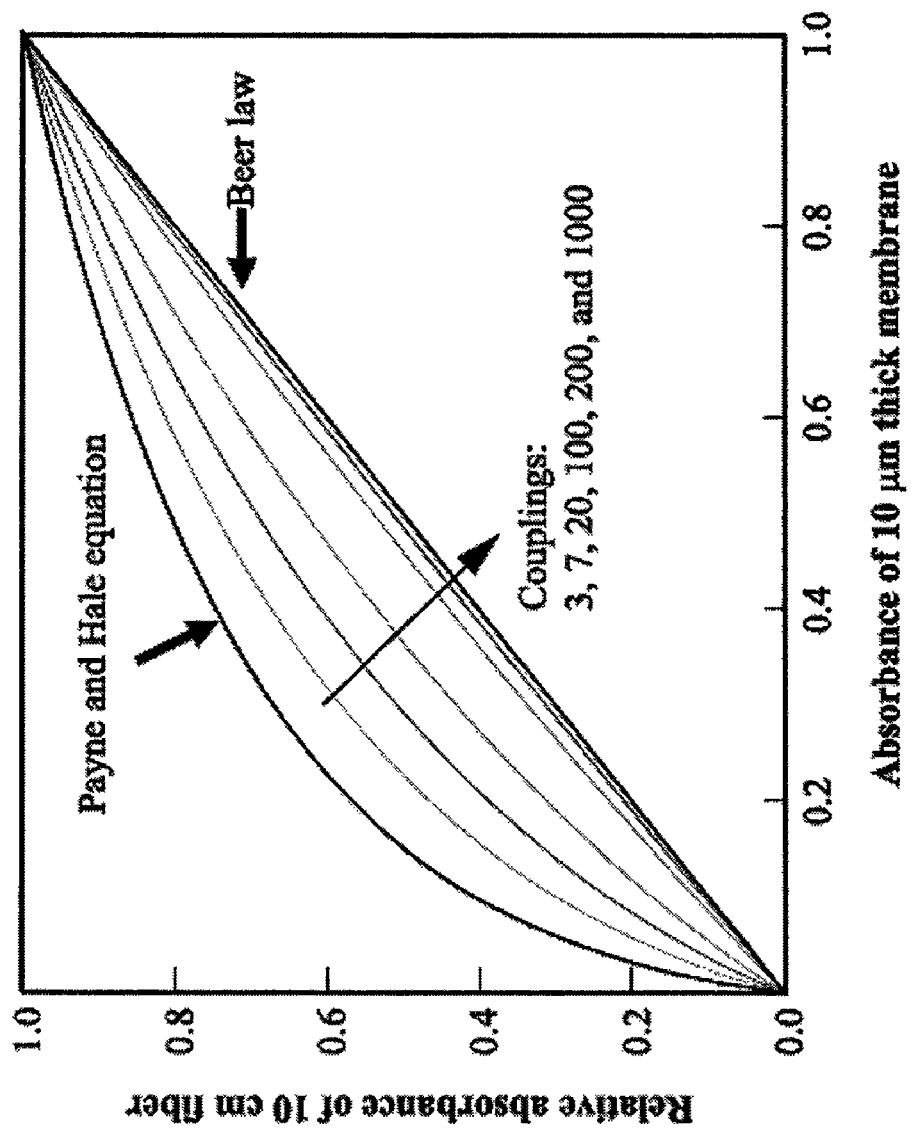
FIG. 2 is a graph showing the simulation of the relationship between the intrinsic absorbance of the cladding and the absorbance of a sensing optical fiber of increasing mode coupling.

Now referring to FIG. 2, a theory for multimode evanescent fiber sensors was proposed in Payne, F. P. and Z. M. Hale, "Deviation from Beer's law in multimode optical fiber evanescent field sensors.", International Journal of Optoelectronics, 8, 743, 1993. It considers an ideal step-index single-clad fiber with an absorbing cladding of infinite thickness. Based on analytical approximations developed for weakly guiding multimode fibers, the absorbance of the sensing optical fiber 10 at a given wavelength $\lambda$ is related to the intrinsic unit length Neperian absorbance $\alpha(\lambda)$ of the material of the cladding 14. The graph of FIG. 2 shows this relationship according to the model of Payne and Hale in a specific case where $\lambda=650$ nm and the numerical aperture NA and the core diameter of the fiber are respectively 0.2 and 400 μm.

It is noted that the model of Payne and Hale assumes no significant mode coupling and a uniform optical power distribution in the propagation modes at the input of the optical fiber 10. Sensing optical waveguides with no significant mode coupling may behave according to this model but are sensitive to input light conditions. These assumptions are not needed in the case of high mode coupling sensing optical fibers.

Mode Coupling Model

An approximate model of mode coupling along the optical fiber 10 can be provided by dividing the optical fiber 10 into n sections of sub-lengths L/n, where L is the total length of the optical fiber 10. According to a simplified model, it is then assumed that the output power of each section is redistributed uniformly between the modes before entering the next section. Hence, each fiber section can be described by the Payne and Hale's model applied for a fiber of length L/n. The modified overall transmittance $T'(\lambda)$ is then simply given by the multiplication of the n individual transmittances:

$$T'(\lambda, L) = [T(\lambda, L/n)]^n. \qquad (1)$$

The higher the value of n, the more important the mode coupling is. For high values of n, it can be demonstrated that the transmittance of the multimode evanescent wave optical fiber 10 is given by a modified Beer-Lambert law, namely:

$$T'(\lambda) \approx e^{-\alpha(\lambda)\eta(\lambda)L}, \qquad (2)$$

where $\alpha(\lambda)$ is the unit length absorption spectrum of the cladding 14 and $\eta(\lambda)$ is the fraction of the total optical power propagating in the cladding.

FIG. 2 shows the relationship between the intrinsic absorbance of the cladding 14 and the absorbance (defined as $-\log(T'(\lambda))$) of the sensing optical fiber 10 with an increasing number of sections n, i.e. for increasing mode coupling. Both the abscissa and the ordinate of the graph of FIG. 2 have been normalized for better understanding. It shows that in the case of strong mode coupling, there is a linear relationship between the intrinsic absorbance of the cladding 14 and the absorbance of the sensing optical fiber 10. The modified Beer-Lambert law (eq. 2) is then valid. Accordingly, contrarily to the requirements for most fiber optic applications, high mode coupling is preferable in the case of the present evanescent wave sensing optical fiber and sensor.

For the sensing optical fiber 10 to respond according to the Beer-Lambert law, i.e. to provide a linear relationship between the absorbance of the sensing optical fiber 10 and the absolute concentration of any state of the indicator in the cladding, the optical fiber 10 should follow a strong mode coupling regime.

The mode coupling length (Lc) of a multimode optical fiber is the length over which an equilibrium mode distribution is achieved. This length is inversely proportional to the coupling coefficient D as defined by the following power-flow equation describing the evolution of the angular content $P(\theta,z)$ of a multimode optical beam propagating in a optical fiber that shows mode coupling:

$$\frac{\partial P(\theta, z)}{\partial z} = -\gamma(\theta)P(\theta, z) + \frac{D}{\theta}\frac{\partial P(\theta, z)}{\partial \theta} + D\frac{\partial^2 P(\theta, z)}{\partial \theta^2},$$

where $\theta$ is the angle of a ray with respect to the propagation axis Z and $y(\theta)$ is the angle-dependent attenuation. As the beam propagates along the fiber, the different mechanisms causing mode coupling induce a diffusion of the angular content as suggested by the light diffusion equation (3) above. Beyond the mode coupling length Lc, the angular distribution $P(\theta)$ becomes essentially independent of the initial angular components injected into the fiber. The coupling length is determined from the mode coupling coefficient D which can be measured as described in S. Savovic and A. Djordjevich, "Method for calculating the coupling coefficient in step-index optical fibers", Applied Optics, 46, 1477 (2007).

The coupling length Lc should be small for the absorption of the sensor described herein to follow a simple Beer-Lambert law. More specifically, the coupling length should be much shorter than the sensing length of the sensing optical fiber of the sensor. FIG. 2 suggests, for example, a factor of more than twenty or so, and, if possible, of more than one hundred, for a Beer-Lambert-like behavior of the sensor.

Coupling lengths of mode coupling optical fibers typically range from a few millimeters to a few meters, depending on the coupling coefficient D which itself depends on the particular coupling mechanism(s) involved. Considering typical sensing optical fiber lengths of 2 to 10 centimeters for in-solution ion detection sensors, coupling lengths shorter than about 5 millimeters or so are suitable for such applications. Coupling lengths shorter than about 1 millimeters is preferable for sensing lengths in the low range. It is noted that in other applications, as will be discussed herein below, the sensing optical fiber can be longer and so can be the coupling length Lc.

Ion-Selective Sensing Cladding

As explained hereinabove, in the present embodiment, the sensing cladding 14 of the sensing optical fiber 10 comprises a light-absorbing indicator directly or indirectly providing the optical response to a given chemical or to given chemicals. Direct sensitivity refers to an indicator which is directly in a chemical equilibrium with the analyte. The simplest example of a direct sensitivity is a pH indicator in a pH optode. Indirect sensitivity refers to a chemical equilibrium between the indicator and the analyte which is carried on by many chemical intermediates which are in equilibrium with each other. Such a more complex mechanism is schematized by the example below.

The matrix material of the ion-selective cladding 14 is prepared from a plasticized or plasticizer-free polymer having thermoplastic properties. For example, the cladding 14 can be prepared from plasticized polyvinyl chloride (PVC). The cladding 14 further contains a chromoionophore/indicator C, i.e. a lipophilic pH indicator, an ion-selective ionophore L, and ionic sites R. The chromoionophore C provides the optical response of the sensing cladding 14, the ionophore L provides the chemical selectivity, and the ionic sites provide electroneutrality by providing charge conservation in the cladding material. The working principle of this membrane is based on a reversible ionic-exchange between analyte ions $M^+$ in solution and hydrogen ions $H^+$ in the sensing cladding 14, and follows:

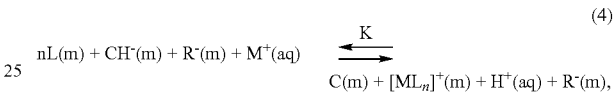
(4)

$$nL(m) + CH^+(m) + R^-(m) + M^+(aq) \rightleftharpoons^{K} C(m) + [ML_n]^+(m) + H^+(aq) + R^-(m),$$

where n is the stoichiometry of the ion-ligand complex $[ML_n]^+$, (m) means that the substance is the in cladding 14 and (aq), in the aqueous sample solution. K is the chemical equilibrium constant. This ionic exchange directly affects the equilibrium between the two chromoionophore states in the cladding 14, namely the protonated state $CH^+$ and the deprotonated state C. Since $CH^+$ and C have different colors, a change in their relative concentration can be quantified using spectroscopic techniques. The relative concentration of the deprotonated state is referred to as the degree of deprotonation $(1-x)$ and is given by:

$$1 - x = \frac{[C]}{[C] + [CH^+]}. \quad (5)$$

The degree of deprotonation $(1-x)$ is related to the concentration—or, to be exact, to the activity—of the target ion in the sample solution 16. This relation depends on the chemical equilibriums in the cladding 14. For instance, for the example given in FIGS. 3-5, the activity a of the analyte and the degree of deprotonation are related by this equation:

$$a = \frac{1}{zK}\frac{x10^{-pH}}{1-x}\frac{[R] - (1-x)([C] + [CH^+])}{\left[[L] - ([R] - (1-x)([C] + [CH^+]))\left(\frac{n}{z}\right)\right]^n}, \quad (6)$$

where [X] is the concentration of compound X, n=z=2 in this particular case and K is the equilibrium constant obtained by calibration. More details can be found in K. Seiler, "Ion-Selective Optode Membranes", Fluka Chemie AG, Buch, 1993, p. 16-24.

The ionic sites R present in the cladding 14 allows an ionic exchange providing cationic/anionic selectivity of the cladding due to the salt structure, i.e., lipophilic anion or cation remaining in the cladding 14 and exchangeable counter ion, cation or anion. The selectivity of ionic exchange of the ionic sites R is dictated by the lipophilicity of the exchangeable ions. Due to the cladding electroneutrality, the number of cations/anions that can enter the cladding 14 does not exceed the concentration of the respective ionic sites. In turn, the ionophore L modulates the selectivity of the ionic exchange provided by the ionic sites R by means of reversible selective binding/complexation of the target ion. In order to provide dominating complexation-determined cladding selectivity, the concentration of the ionophore is selected to be higher than that of the ionic sites.

The ion-selective sensing cladding 14 can be prepared from either plasticized or plasticizer-free polymers. Example of suitable polymeric matrices are: poly(vinyl chloride) (PVC) plasticized with bis(2-ethylhexyl) adipate (DOS), i.e. PVC:DOS; a copolymer of methyl methacrylate (MMA) and n-decyl methacrylate(DMA-MMA); or a copolymer of methyl methacrylate and n-butyl acrylate (BA-MMA). PVC-DOS can be prepared from commercially available products. DMA-MMA can be prepared as described in U.S. Patent Application Pub. No. 2003/0217920 A1 to Peper et al. and BA-MMA can be prepared as described in International Publication No. WO 00/54039 to Hall.

One example of suitable chromoionophore C is ETH 5294. Examples of suitable ionophores L are $Ca^{2+}$ selective ionophore ETH 1001 and $K^+$-selective ionophore valinomycin. Finally, ionic sites can be provided by, for example, sodium tetrakis[3,5-bis(trifluoromethyl)phenyl]borate (NaTFPB). An evanescent wave optical fiber 10 sensitive to a different ion can be obtained by selecting a different appropriate ionophore.

Manufacturing of the Fiber

An evanescent wave optical fiber 10 can be manufactured using different processes. One possible process consists of coating a layer of cladding 14 on an available optical fiber core 12. Coating can be integrated to the drawing process of the core 12 by coating the core 12 continuously during fiber drawing. The coating may also be deposited after the fiber's core has been drawn. The coating can also be applied later on, on an available core 12 of optical fiber. For example, the existent cladding of an available plastic optical fiber can be removed along a given section. The bare core is then coated with a sensing cladding 14 along that section. Coating of the core 12 is preferred when the materials used for making the core 12 and the cladding 14 have incompatible glass transition temperatures, or drawing temperatures. It is however noted that the obtained cladding 14 should be thin enough to provide a suitable time response. Indeed, the evanescent wave interacts with the few micrometers of cladding that are close to the core 12. The thinner the cladding 14, the faster the chemical equilibrium will be achieved between the cladding 14 and the sample solution 16 upon a variation in the composition of the sample solution 16 and the faster will be the response of the sensing optical fiber 10.

In one embodiment, a coating of ion-selective polymeric cladding 14 is deposited on the optical fiber core 12 from a tetrahydrofuran (THF) solution of the selected cladding composition. Drying of the coating solution provides a plastic optical fiber 10 coated with the sensing cladding 14.

If the cladding and core materials have the same thermoplastic properties, the optical fiber 10 can be drawn in a manner similar to that used for standard manufacturing of optical fibers. The optical fiber 10 can then be directly drawn from an optical fiber preform consisting of an optical core rod and a sensitive optical cladding layer. For example, a layer of sensing cladding can be coated on a PMMA rod in order to provide the fiber preform. PMMA being a thermoplastic polymer, an optical fiber can be drawn at a drawing temperature low enough to avoid degradation of the components of the ion-selective cladding material.

Drawing a fiber from a sensing cladding-coated preform allows the production of a large quantity of optode sensing parts in a single step. The preparation of the sensor is then reduced to the connection of the sensing fiber 10 to the remaining components of the optical sensing system. From a 10 cm-long preform having a diameter of 1 cm, one can produce 62.5 meters of optical fiber having a diameter of 400 µm, or 625 10 cm-long optode sensing parts. Due to the short length of optical fiber required to make an optode, low optical quality material can be used as, for example, commercially available Plexiglas® with typical intrinsic attenuation of 1.5 to 5 dB/m in the wavelength range of 400 to 700 nm. The resulting 10 cm-long optodes have a core attenuation of about 0.2 to 0.5 dB which is fine for most practical applications.

Planar or channel sensing optical waveguides can also be manufactured by spin-coating a planar substrate with the selected cladding cocktail dissolved in a suitable solvent. Thin cladding membrane, 4 µm-thick for example, can be achieved using such methods.

EXAMPLE 1

Manufacturing by Preform Drawing

In one embodiment, the core of the preform is made from a commercial rod of Plexiglas® having a diameter of 11 mm with a refractive index $n^{20}_D$ of 1.491 and a glass transition temperature Tg of about 108-109° C. The preform is prepared by multiple constant-speed immersions of the Plexiglas® rod into a solution of the selected cladding material compound until the desired layer thickness is reached on the perform. In this case, the cladding matrix is made of a copolymer poly (methyl methacrylate-co-decyl methacrylate) (pMMA-DMA) ($n^{20}_D$=1.476) synthesized in benzene. The pMMA-DMA-based cladding cocktail also comprises chromoionophore ETH 5294, anionic sites tetrakis[3,5-bis (trifluoromethyl)phenyl]borate sodium (NaTFPB), and potassium-selective ionophore valinomycin using tetrahydrofuran as the solvent. Fiber drawing is performed at a furnace temperature of 200° C. In those conditions, preform temperature does not exceed 180° C. but maintains this temperature for a few minutes.

EXAMPLE 2

Figure 3:
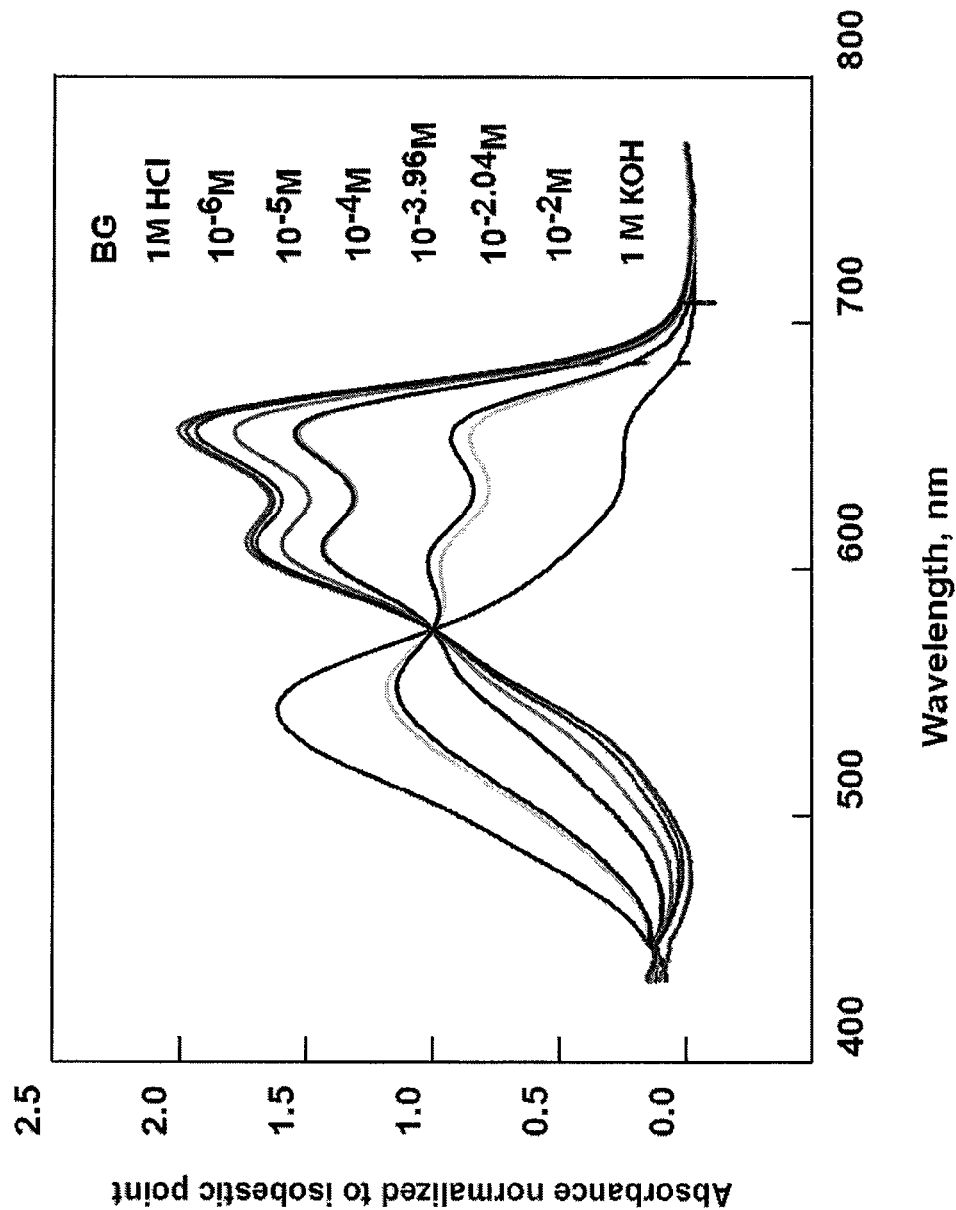
FIG. 3 is a graph showing the optical absorption spectra of a $Ca^{2+}$-selective optical fiber with varying concentrations of $Ca^{2+}$ ions.
Figure 4:
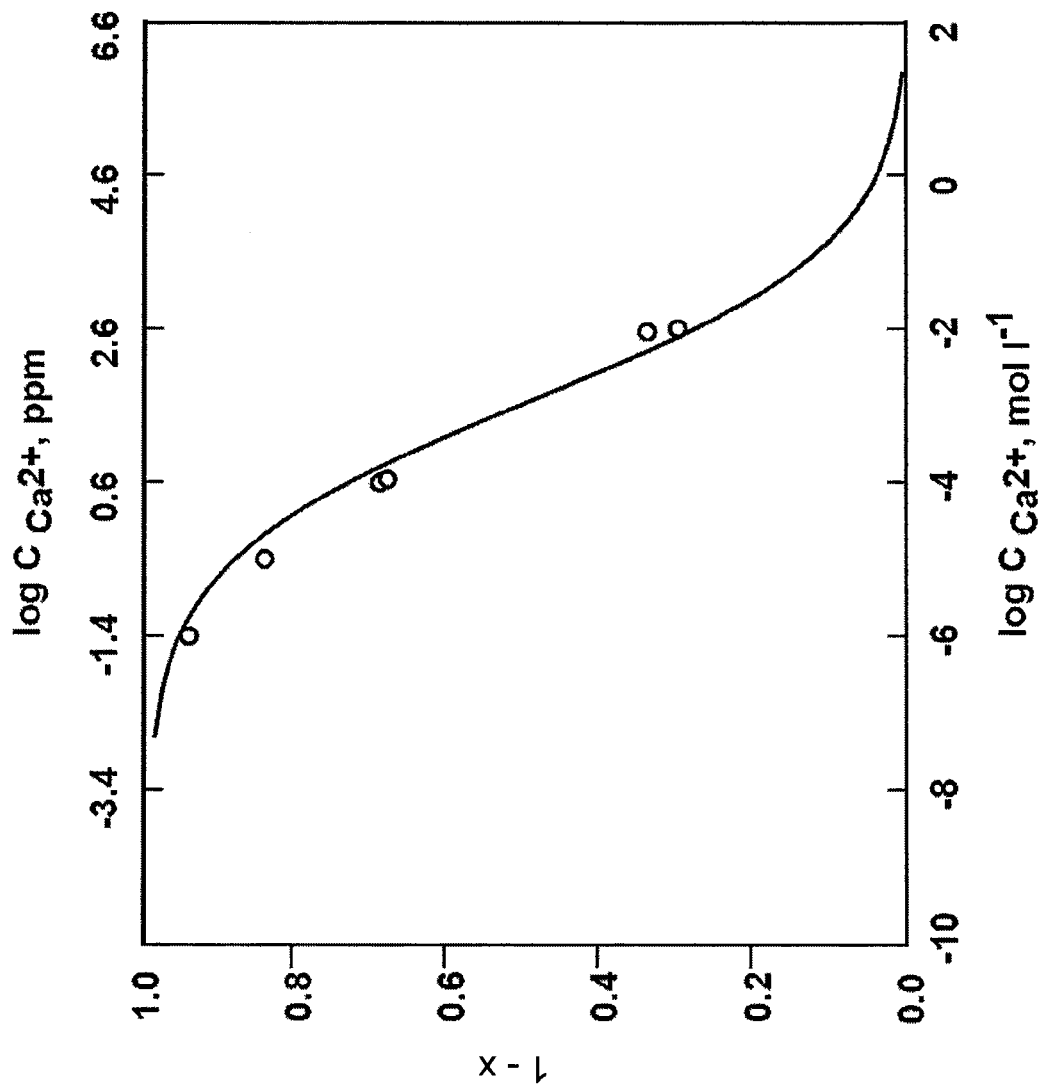
FIG. 4 is a graph showing the calibration curve of the $Ca^{2+}$-selective optical fiber of FIG. 3.

FIG. 3 shows experimental optical absorption spectra illustrating the sensitivity of an optical fiber having a $Ca^{2+}$-selective nBA-MMA cladding painted on a bare PMMA fiber core. The different curves show the optical spectra of the fiber obtained when immersed in solutions of various concentrations of $CaCl_2$. The spectra are baseline-corrected and normalized to the isobestic wavelength of 571 µm. FIG. 4 shows the calibration curve of the $Ca^{2+}$-selective optical fiber and FIG. 5 shows the time response of the $Ca^{2+}$ selective optical fiber.

The $Ca^{2+}$-selective optical fiber under test is made from a Plexiglas® fiber core drawn, using drawing techniques known in the art, from a 10 cm Plexiglas® (PMMA) rod having a 10 mm diameter. A 400 µm optical fiber core is obtained. A 10 cm-long section of optical fiber core is then coated by painting a solution of the polymeric cladding mixture dissolved in tetrahydrofuran to provide the sensing cladding. A dried coating of approximately 4 µm is obtained. In this example, the cladding mixture contains a matrix nBA- MMA, ionic sites NaTFPB 12.26 mmol/kg, ionophore ETH 1001 40.23 mmol/kg and chromoionophore I ETH 5294 9.47 mmol/kg.

Figure 5:
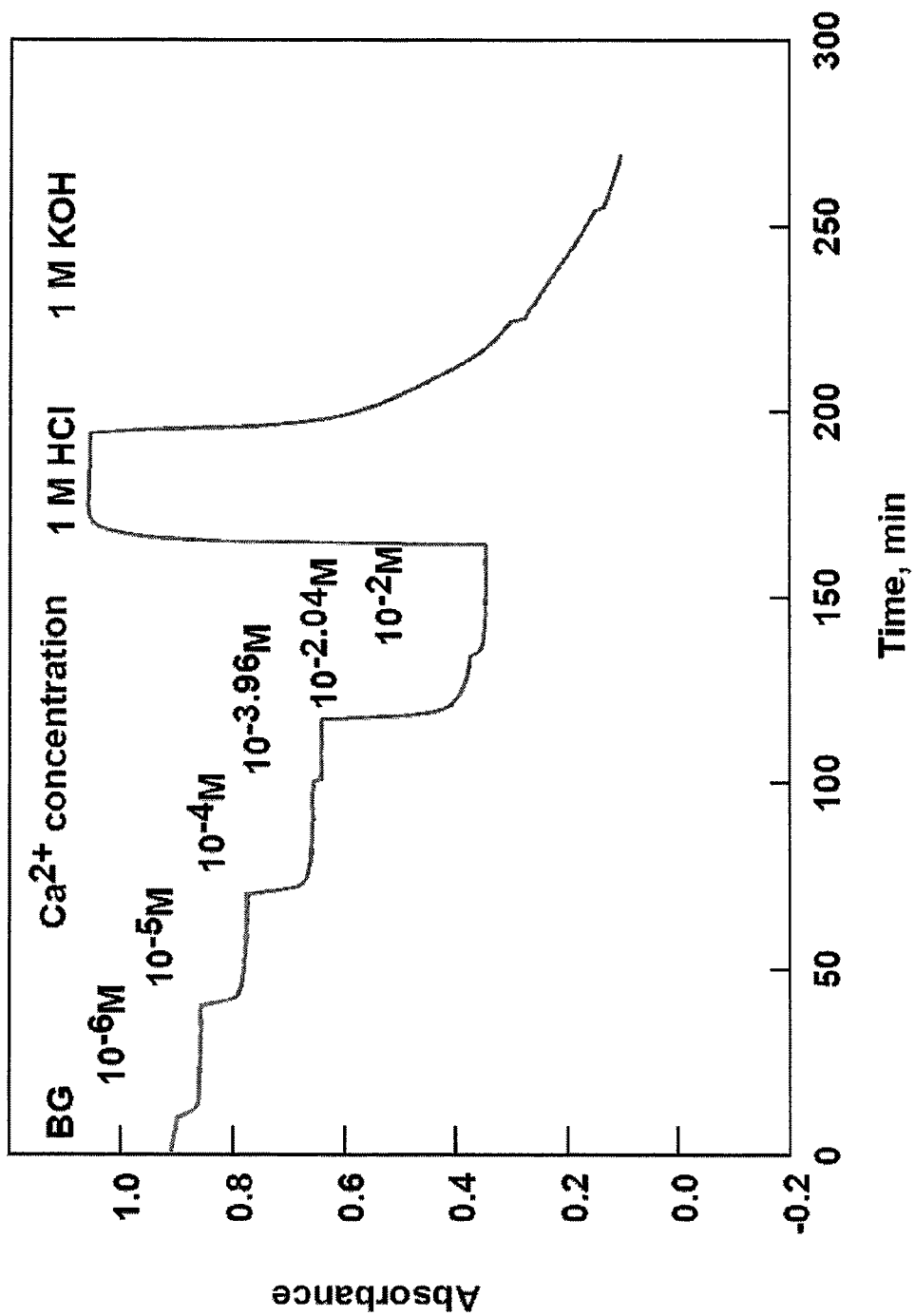
FIG. 5 is a graph showing the time response of the $Ca^{2+}$-selective optical fiber of FIG. 3.

FIGS. 3-5 show experimental results obtained with aqueous solutions of 1M HCl and 1M KOH (absorbance spectra of all protonated and all deprotonated chromoionophore, respectively) and sample solutions containing $10^{-6}$ M to $10^{-2}$ M $CaCl_2$, and a constant buffer background of 0.05 M TRIS-HCl pH 7.

Figure 6:
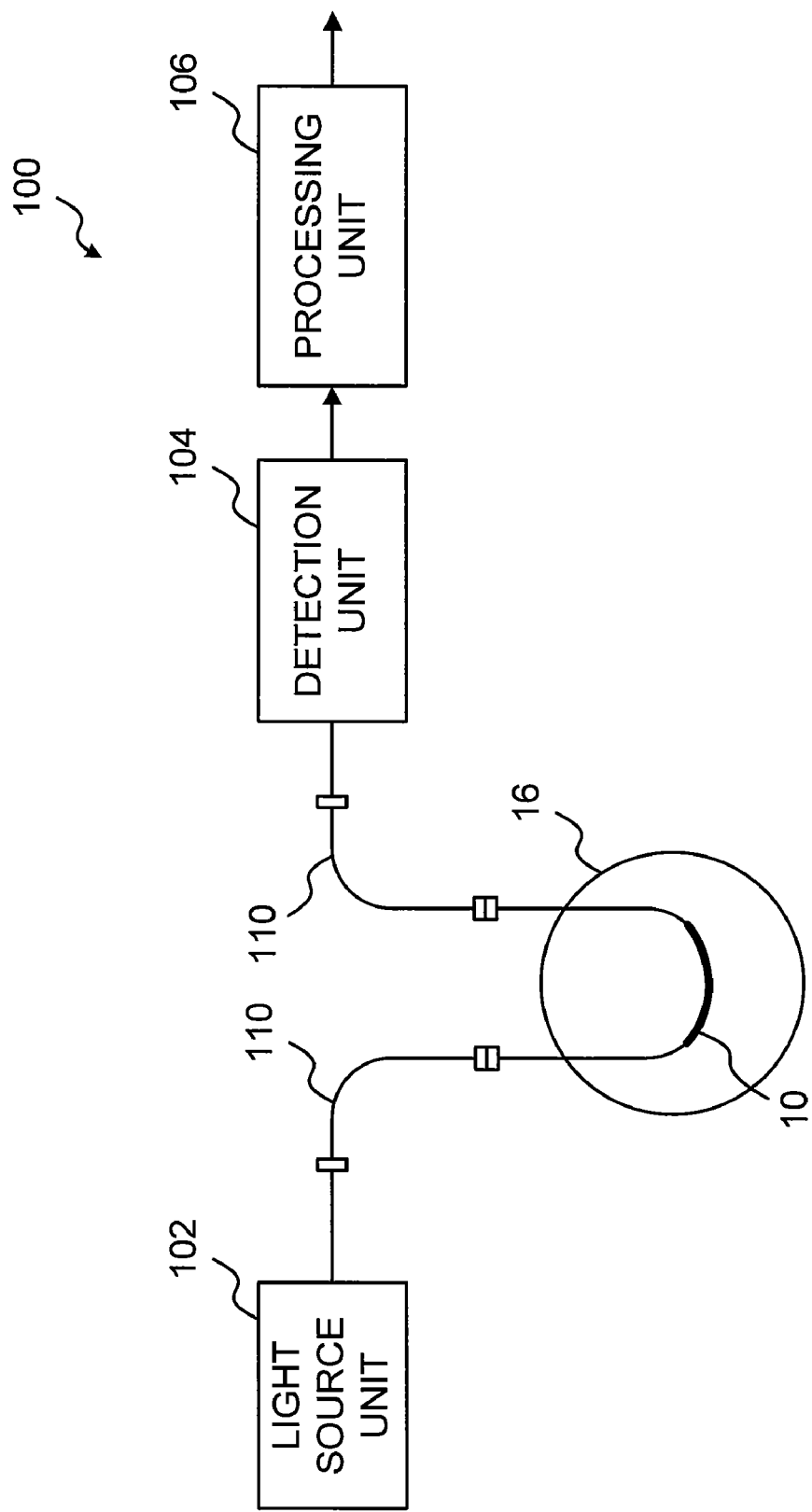
FIG. 6 is a block diagram illustrating an evanescent wave multimode optical waveguide sensor comprising the optical fiber of FIG. 1, wherein the sensing optical fiber is used in transmission.
Figure 7:
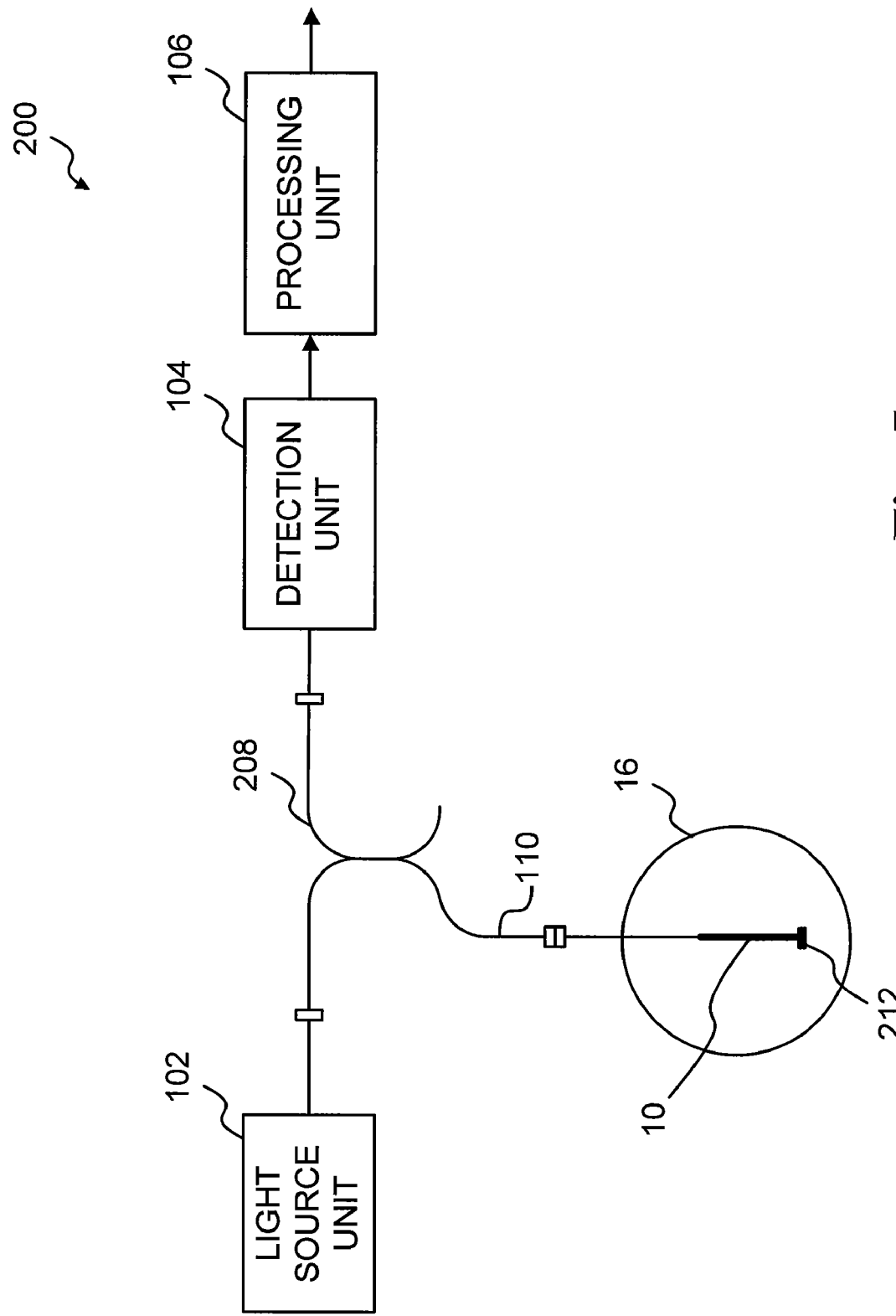
FIG. 7 is a block diagram illustrating an evanescent wave multimode optical waveguide sensor comprising the optical fiber of FIG. 1, wherein the sensing optical fiber is used in reflection.

FIG. 6 illustrates an evanescent wave multimode optical fiber sensor 100 using the sensing fiber 10 in a transmission configuration while FIG. 7 illustrates an optical fiber sensor 200 using the sensing fiber 10 in a reflection configuration. Both configurations comprise a light source unit 102 and a detection unit 104 for measuring the transmission spectrum of the sensing optical fiber 10 over a useful bandwidth for detection of a variation in the absorption of the sensing optical fiber 10 due to the change of concentration of a chemical species in the sample solution 16. The light source unit 102 provides the light to be propagated in the optical fiber 10 and the detection unit 104 detects the light propagated in the optical fiber 10 after a one-way transmission in the case of the configuration of FIG. 6 and after one back and forth transmission in the case of the configuration of FIG. 7. The absorption spectrum of the optical fiber 10 is then measured.

In one embodiment, the light source unit 102 is a broadband white light source and a fiber optics spectrophotometer is used as the detection unit 104 but one should appreciate that a tunable broadband light source and an optical detector could be used instead. A broadband analysis provides the absorption spectrum of the optical fiber 10 but it is noted that the absorbance of the optical fiber 10 could also be measured at a single wavelength representative of the variation of the absorbance of the fiber 10 related to the concentration of the analyte (or to the physical parameter) to be measured. A measurement at a second wavelength can additionally be provided as a reference. For example, the light source unit 102 comprises two or more single-wavelength sources combined before light injection to the sensing optical fiber 10. The detection unit may then comprise an optical wavelength division coupler for splitting the two wavelengths from light collected from the sensing optical fiber 10 and two optical detectors for detecting the optical power at each split wavelength.

In all cases, both sensors 100 and 200 comprise a processing unit 106 for determining the concentration of the chemical species to be sensed from the measured optical absorbance of the sensing optical fiber 10 according to prior calibration. As described hereinabove, the absorption of the sensing optical fiber 10 follows a law similar to the Beer-Lambert law and a measurement of the sensed parameter can be retrieved accordingly.

In one embodiment, light from the light source unit 102 and to the detection unit 104 is injected and collected from the sensing optical fiber 10 using a 400 µm silica fiber 110 with a numerical aperture of 0.22. Coupling of the silica injection and collection optical fibers 110 to the sensing optical fiber 10 is made by gluing it with UV-curable fluoroacrylate inside a Teflon™ tube tightly fitted about the silica and sensing optical fibers.

In the embodiment of FIG. 6 both ends of the sensing fiber 10 are connected, while in the embodiment of FIG. 7, only one end of the sensing fiber 10 has an optical connection. In the embodiment of FIG. 7, light is injected and collected in the sensing fiber 10 from the same end, propagated light being reflected at the opposed end of the sensing fiber 10 using a reflection coating 212. Light is then directed from the light source unit 102 to the sensing fiber 10 and from the sensing fiber 10 to the detection unit 104 using an optical coupler 208, for example.

Figure 8:
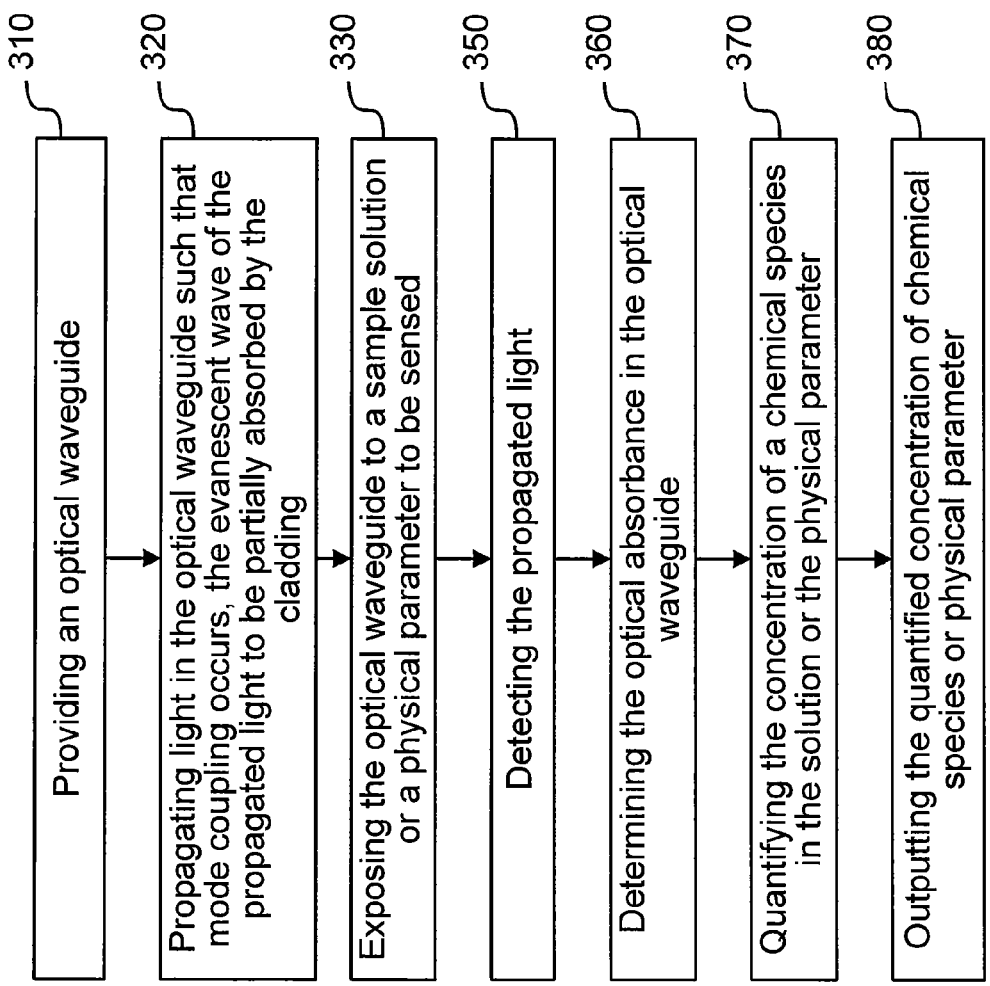
FIG. 8 is a flow chart illustrating a method for sensing a chemical species or a physical parameter.

FIG. 8 illustrates a method for sensing a chemical or a physical parameter using, for example, one of the evanescent wave multimode optical fiber sensors described hereinabove. In step 310, an optical waveguide is provided. The optical waveguide has an optical waveguide core and a cladding for guiding light to be propagated in the optical waveguide. For example, the optical fiber 10 can be used. In step 320, light is propagated in the optical waveguide such that mode coupling occurs in the optical waveguide while light propagates. Mode coupling is produced, for example, by using a waveguide core made of an heterogeneous material. The evanescent wave of light which propagates in the cladding is to be partially absorbed by the cladding. In step 330, the optical waveguide is exposed to a sample solution containing the chemical species or to a physical parameter to be sensed to produce a variation of the optical absorption of the cladding. As described above, the optical absorption can be varied using an indicator provided in the cladding and directly or indirectly sensitive to the change of concentration of the chemical species or to the physical parameter. The evanescent wave is partially absorbed by the cladding according to the variable optical absorption of the cladding. In step 350, light propagated in the optical waveguide is detected using, for example, the detection unit 104. In step 360, the optical absorbance of the light in the optical waveguide is determined from the detected light. In step 370, the concentration of the chemical species or physical parameter to be determined is quantified from the optical absorption making use of a pseudo Beer-Lambert law and the involved equilibrium between the indicator and the analyte concentration or the physical parameter to be determined. Finally, in step 380, the quantified chemical concentration or physical parameter is outputted for use in monitoring the chemical species or the physical parameter. For example, the quantified value can be simply displayed or can be numerically outputted to be recorded or analyzed by an external device.

While the invention is illustrated herein with embodiments for sensing a concentration of an analyte in a solution, a physical parameter can also be sensed using an indicator sensitive to temperature (thermochromism), solvent vapor detection (solvatochromism), current (electrochromism), ion (ionochromism), pH (halochromism), pressure (piezochromism), etc. The sensing cladding is then made of a matrix material such as a plasticized polymer, a plasticizer-free polymer or any other suitable non-polymer material, to which the suitable indicator is added.

It is noted that not only ions but also neutral chemical species can be analyzed using an evanescent wave multimode optical waveguide as described herein. For instance, a concentration of an alcohol can be analyzed making use of chromoreactant CR-546 from Fluka as the indicator.

It is also noted that, in addition to aqueous solutions, non-aqueous solutions and gaseous mixtures can be analyzed using an evanescent wave multimode optical waveguide as described herein. Depending on the sample media and the sensor exposure/lifetime requirements, the properties of the materials used in the core and the sensing cladding are adjusted for the specific application.

It is also noted that the light absorption of the analyte that absorbs in UV/Vis-range can be directly measured without resort to an indicator, by rather using direct spectroscopy. For example, the cladding can be made of a permeable material which can be impregnated by a light absorbing neutral analyte through partitioning. When the sensor is immersed in a solution containing the chemicals, the concentration of the chemicals can then be directly determined by direct spectroscopy provided that the optical fiber shows mode coupling strong enough to provide reproducible results.

One major application of the proposed sensing waveguide and sensor is for chemical sensors, namely ion-selective sensors. The proposed sensing waveguide and sensor can be used in the preparation of disposable/exchangeable and inexpensive key elements of the optical sensors. The proposed sensing waveguide and sensor provides insensitivity to the color and turbidity of the sample solution and fairly low cost per sensing unit.

The embodiments of the invention described above are intended to be exemplary only. The scope of the invention is therefore intended to be limited solely by the scope of the appended claims.

What is claimed is: ,

1. An evanescent wave multimode optical waveguide sensor for measuring at least one of a chemical species and a physical parameter, the sensor comprising:
   an optical waveguide having an optical waveguide core with a core refractive index and a cladding, surrounding said core, with a cladding refractive index, for guiding light to be propagated, said optical waveguide having:
      a sensing portion with a cladding refractive index lower than said core refractive index such that an evanescent wave of said light propagates in said cladding, said cladding comprising a chromoionophore providing an optical absorption varying as a function of said at least one of a chemical species and a physical parameter, said evanescent wave to be at least partially absorbed by said cladding due to said optical absorption, said sensing portion further being provided with mode coupling means having a mode coupling length which is substantially shorter than a length of said sensing portion for causing continuous redistribution between propagation modes, along said sensing portion, of unabsorbed light power of said light as said light propagates;
   a light source unit connected to said optical waveguide for providing said light to be propagated in said optical waveguide;
   a detection unit connected to said optical waveguide for detecting said light propagated in said optical waveguide for determining an optical absorbance of said light in said optical waveguide; and
   a processing unit associated with said detection unit for determining said at least one of a chemical species and a physical parameter from the determined optical absorbance.

2. The optical waveguide sensor as claimed in claim 1, wherein said chromoionophore is chemical indicator to be involved in a reversible chemical equilibrium resulting in the variation of said optical absorption of said cladding with said chemical species.

3. The optical waveguide sensor as claimed in claim 1, wherein said mode coupling means is said core being made of a heterogeneous material to provide said mode coupling.

4. The optical waveguide sensor as claimed in claim 1, wherein said mode coupling means is said optical waveguide comprising microcurvatures to provide said mode coupling.

5. The optical waveguide sensor as claimed in claim 1, wherein said cladding comprises a polymeric material.

6. The optical waveguide sensor as claimed in claim 2, wherein said cladding comprises a matrix material, the chromoionophore, an ion-selective ionophore, and ionic sites.

7. The optical waveguide sensor as claimed in claim 1, wherein said optical waveguide is an optical fiber.

8. The optical waveguide sensor as claimed in claim 1, wherein said mode coupling length is at least one hundred times smaller than said length of said sensing portion.

9. A method for determining at least one of a concentration of a chemical species in a sample solution and a physical parameter, the method comprising:
   providing an optical waveguide having an optical waveguide core with a core refractive index and a cladding surrounding said core, with a cladding refractive index, for guiding light to be propagated in said optical waveguide said optical waveguide having a sensing portion with a cladding refractive index lower than said core refractive index such that an evanescent wave of said light propagates in said cladding, said cladding comprising a chromoionophore providing an optical absorption of said cladding varying as a function of said at least one of a chemical species and a physical parameter, said evanescent wave to be at least partially absorbed by said cladding due to said optical absorption, said sensing portion further being provided with mode coupling means having a mode coupling length which is substantially shorter than a length of said sensing portion for causing continuous redistribution between propagation modes, along said sensing portion, of unabsorbed light power of said light as said light propagates;
   propagating light in said optical waveguide such that mode coupling occurs in said optical waveguide while said light propagates, an evanescent wave of said light propagating in said cladding to be at least partially absorbed by said cladding;
   exposing said optical waveguide to at least one of said sample solution and said physical parameter to produce a variation of an optical absorption of said cladding;
   detecting said light propagated in said optical waveguide;
   determining an optical absorbance in said optical waveguide from the detected light;
   quantifying at least one of said concentration of said chemical species and said physical parameter from the determined optical absorbance; and
   outputting at least one of the quantified concentration of said chemical species and the quantified physical parameter.

10. The method as claimed in claim 9, wherein said chromoionophore is a chemical indicator directly or indirectly sensitive to said chemical species for varying said optical absorption.

11. The method as claimed in claim 9, wherein said quantifying comprises quantifying a degree of deprotonation of said chromoionophore from the determined optical absorbance using a Beer-Lambert law, and determining at least one of said concentration of said chemical species and said physical parameter using the quantified degree of deprotonation.

12. The sensor as claimed in claim 3, wherein said heterogeneous material comprises a polymer.

13. The sensor as claimed in claim 12, wherein said heterogeneous material comprises a poly(methyl methacrylate).

14. The sensor as claimed in claim 2, wherein said indicator comprises a pH indicator.

15. The sensor as claimed in claim 1, wherein said optical waveguide has a mode coupling length of less than 5 millimeters.

* * * * *